(12) United States Patent
Stoltenberg

(10) Patent No.: US 11,857,228 B2
(45) Date of Patent: Jan. 2, 2024

(54) SET SCREW FOR FEMORAL NAIL

(71) Applicant: Stryker European Operations Limited, Carrigtwohill (IE)

(72) Inventor: Ingo Stoltenberg, Probsteierhagen (DE)

(73) Assignee: Stryker European Operations Limited

( * ) Notice: Subject to any disclaimer, the term of this patent is extended or adjusted under 35 U.S.C. 154(b) by 0 days.

(21) Appl. No.: 17/909,059

(22) PCT Filed: Mar. 3, 2021

(86) PCT No.: PCT/IB2021/000114
§ 371 (c)(1),
(2) Date: Sep. 2, 2022

(87) PCT Pub. No.: WO2021/176272
PCT Pub. Date: Sep. 10, 2021

(65) Prior Publication Data
US 2023/0086656 A1 Mar. 23, 2023

Related U.S. Application Data

(60) Provisional application No. 62/985,981, filed on Mar. 6, 2020.

(51) Int. Cl.
*A61B 17/74* (2006.01)
*A61B 17/88* (2006.01)

(52) U.S. Cl.
CPC ........ *A61B 17/744* (2013.01); *A61B 17/8897* (2013.01)

(58) Field of Classification Search
CPC .......................... A61B 17/744; A61B 17/8897
(Continued)

(56) References Cited

U.S. PATENT DOCUMENTS 3,433,220 A 3/1969 Zickel
4,776,330 A 10/1988 Chapman et al.
(Continued)

FOREIGN PATENT DOCUMENTS

CA 2986540 A1 12/2016
EP 0257118 B1 6/1990
(Continued)

OTHER PUBLICATIONS

European Examination Report for Application No. 12705227.2 dated May 5, 2015.
(Continued)

*Primary Examiner* — Eduardo C Robert
*Assistant Examiner* — Tara Rose E Carter
(74) *Attorney, Agent, or Firm* — Lerner David LLP

(57) ABSTRACT

An intramedullary intertrochanteric fracture fixation device includes an intramedullary nail having a proximal portion and a distal portion, a neck screw and a set screw assembly (264, 262, 266). The intramedullary nail defines an angulated opening in the proximal portion and includes an axial bore extending through a proximal end of the nail and into the angulated opening. The proximal portion further includes a compartment defined by an upper stop, a lower stop and a sidewall. The sidewall of the compartment defines a slot. The neck screw is insertable the angulated opening and includes a length and an exterior surface defining a groove. The set screw assembly (264, 262, 266) is pre-operatively assembled within the proximal portion of the intramedullary nail and selectively moveable into the compartment for preventing rotational movement of the neck screw within the angulated opening of the intramedullary nail. The set screw is cannulated to receive a guidewire when pre-operatively assembled.

13 Claims, 9 Drawing Sheets

(58) Field of Classification Search
USPC .................................................. 606/62–68
See application file for complete search history.

(56) References Cited

U.S. PATENT DOCUMENTS

| | | | |
|---|---|---|---|
| 5,032,125 A | 7/1991 | Durham et al. | |
| 5,176,681 A | 1/1993 | Lawes et al. | |
| 5,454,813 A | 10/1995 | Lawes | |
| 6,221,074 B1 | 4/2001 | Cole et al. | |
| 6,296,645 B1 | 10/2001 | Hover et al. | |
| 6,402,753 B1 | 6/2002 | Cole et al. | |
| 6,406,477 B1 | 6/2002 | Fujiwara | |
| 6,443,954 B1 | 9/2002 | Bramlet et al. | |
| 6,648,889 B2 | 11/2003 | Bramlet et al. | |
| 6,835,197 B2 | 12/2004 | Roth et al. | |
| 6,855,146 B2 | 2/2005 | Frigg et al. | |
| 6,921,400 B2 | 7/2005 | Sohngen | |
| 6,926,719 B2 | 8/2005 | Sohngen et al. | |
| 7,018,380 B2 | 3/2006 | Cole | |
| 7,041,104 B1 | 5/2006 | Cole et al. | |
| 7,182,765 B2 | 2/2007 | Roth et al. | |
| 7,306,600 B2 | 12/2007 | Roth et al. | |
| 7,591,819 B2 | 9/2009 | Zander et al. | |
| 7,601,153 B2 | 10/2009 | Shinjo et al. | |
| 7,763,023 B2 | 7/2010 | Gotfried | |
| 7,867,231 B2 | 1/2011 | Cole | |
| 8,092,454 B2 | 1/2012 | Sohngen | |
| 8,100,911 B2 | 1/2012 | Yamazaki et al. | |
| 8,157,801 B2 | 4/2012 | Doubler et al. | |
| 8,157,802 B2 | 4/2012 | Elghazaly et al. | |
| 8,172,841 B2 | 5/2012 | Defossez | |
| 8,303,590 B2 | 11/2012 | Elghazaly et al. | |
| 8,486,071 B2 | 7/2013 | Jensen et al. | |
| 8,491,584 B1 | 7/2013 | Fagan | |
| 8,702,707 B2 | 4/2014 | Sohngen | |
| 8,808,293 B2 | 8/2014 | Buettler et al. | |
| 8,840,675 B2 | 9/2014 | Song | |
| 8,906,023 B2 | 12/2014 | Matityahu et al. | |
| 8,915,917 B2 | 12/2014 | Doherty et al. | |
| 9,060,808 B2 | 6/2015 | Overes et al. | |
| 9,072,552 B2 | 7/2015 | Simon et al. | |
| 9,084,643 B2 | 7/2015 | Mikhail et al. | |
| 9,149,316 B2 | 10/2015 | Appenzeller et al. | |
| 9,220,544 B2 | 12/2015 | Matityahu et al. | |
| 9,295,504 B2 | 3/2016 | Haidukewych et al. | |
| 9,433,448 B2 | 9/2016 | Ehmke et al. | |
| 9,433,449 B2 | 9/2016 | Vega et al. | |
| 9,463,054 B2 | 10/2016 | Mueckter | |
| 9,526,542 B2 | 12/2016 | Ehmke | |
| 9,597,128 B2 | 3/2017 | Boileau et al. | |
| 9,757,169 B2 | 9/2017 | Boraiah | |
| 9,861,418 B2 | 1/2018 | Matityahu et al. | |
| 9,883,895 B2 | 2/2018 | Mikhail et al. | |
| 9,895,177 B2 | 2/2018 | Hientzsch et al. | |
| 9,918,757 B2 | 3/2018 | Roth et al. | |
| 9,936,989 B2 | 4/2018 | Halder | |
| 9,943,346 B2 | 4/2018 | Elghazaly et al. | |
| 10,092,334 B2 | 10/2018 | Sato et al. | |
| 2002/0032445 A1 | 3/2002 | Fujiwara | |
| 2002/0107578 A1 | 8/2002 | Speitling et al. | |
| 2002/0156473 A1 | 10/2002 | Bramlet et al. | |
| 2004/0127898 A1 | 7/2004 | Adam | |
| 2005/0069397 A1 | 3/2005 | Shavit et al. | |
| 2005/0143739 A1 | 6/2005 | Shinjo et al. | |
| 2005/0203510 A1 | 9/2005 | Sohngen | |
| 2006/0156473 A1 | 7/2006 | Chambers et al. | |
| 2006/0200160 A1 | 9/2006 | Border et al. | |
| 2007/0049938 A1 | 3/2007 | Wallace et al. | |
| 2007/0049939 A1 | 3/2007 | Wallace et al. | |
| 2007/0049940 A1 | 3/2007 | Wallace et al. | |
| 2007/0233100 A1 | 10/2007 | Metzinger | |
| 2008/0140077 A1 | 6/2008 | Kebaish | |
| 2008/0294164 A1 | 11/2008 | Frank et al. | |
| 2008/0294203 A1 | 11/2008 | Kovach et al. | |
| 2009/0048600 A1 | 2/2009 | Matityahu et al. | |
| 2009/0248025 A1 | 10/2009 | Haidukewych et al. | |
| 2010/0249781 A1 | 9/2010 | Haidukewych et al. | |
| 2010/0249852 A1 | 9/2010 | Brumfield et al. | |
| 2011/0054474 A1 | 3/2011 | Metzinger et al. | |
| 2011/0196372 A1 | 8/2011 | Murase | |
| 2012/0197255 A1 | 8/2012 | Elghazaly | |
| 2012/0253410 A1 | 10/2012 | Taylor et al. | |
| 2013/0041414 A1 | 2/2013 | Epperly et al. | |
| 2013/0158601 A1 | 6/2013 | Stone et al. | |
| 2014/0012259 A1 | 1/2014 | Matityahu et al. | |
| 2014/0058392 A1* | 2/2014 | Mueckter | A61B 17/7233 606/64 |
| 2014/0088595 A1 | 3/2014 | Mueckter et al. | |
| 2014/0094802 A1 | 4/2014 | Simon et al. | |
| 2014/0330174 A1 | 11/2014 | Warlick et al. | |
| 2014/0330274 A1 | 11/2014 | Matityahu et al. | |
| 2015/0209090 A1 | 7/2015 | Simon et al. | |
| 2015/0272634 A1 | 10/2015 | Mikhail et al. | |
| 2016/0199109 A1* | 7/2016 | Zehtab | A61B 17/7225 606/64 |
| 2016/0213409 A1 | 7/2016 | Frank et al. | |
| 2016/0296261 A1 | 10/2016 | Elghazaly | |
| 2016/0310176 A1 | 10/2016 | Van Dyke et al. | |
| 2017/0014167 A1 | 1/2017 | Ehmke | |
| 2018/0146992 A1 | 5/2018 | Prien et al. | |
| 2018/0250042 A1 | 9/2018 | Sato et al. | |

FOREIGN PATENT DOCUMENTS

| | | |
|---|---|---|
| EP | 0838199 A1 | 4/1998 |
| EP | 1175872 A2 | 1/2002 |
| EP | 1415605 A1 | 5/2004 |
| EP | 1547534 A2 | 6/2005 |
| EP | 2253285 A1 | 11/2010 |
| EP | 2730243 A1 | 5/2014 |
| FR | 2965471 A1 | 4/2012 |
| JP | H02-21859 A | 1/1990 |
| JP | 3307805 B2 | 7/2002 |
| JP | 2005205201 A | 8/2005 |
| JP | 2005278819 A | 10/2005 |
| JP | 2009148318 A | 7/2009 |
| KR | 100953149 B1 | 4/2010 |
| WO | 02067794 A1 | 9/2002 |
| WO | 02098330 A2 | 12/2002 |
| WO | 03032852 A2 | 4/2003 |
| WO | 03094763 A1 | 11/2003 |
| WO | 2007038560 A1 | 4/2007 |
| WO | 2008001324 A2 | 1/2008 |
| WO | 2012107056 A1 | 8/2012 |
| WO | 2013090859 A1 | 6/2013 |
| WO | 2013134387 A1 | 9/2013 |
| WO | 2015052841 A1 | 4/2015 |
| WO | 2016190842 A1 | 12/2016 |
| WO | 2019024741 A1 | 2/2019 |

OTHER PUBLICATIONS

Gamma3 Long Nail R2, Copyright date 2004, pp. 1-52.
Heineman, et al., "Intra-abdominal Migration of a Lag Screw in Gamma Nailing: Report of a Case", J Orthop Trauma, Dec. 2010, vol. 24, No. 12, pp. e119-e122.
Horas, et al., "Mediale Schenkelhalsschraubendislokation nach Gammanagelosteosynthese einer pertrochantaren Femurmetastase", Feb. 2008, p. 746-748 (English translation of Abstract provided).
International Search Report for Application No. PCT/EP2011/000585 dated Jun. 27, 2011.
International Search Report for Application No. PCT/EP2012/000577 dated May 31, 2012.
International Search Report for PCT/IB2021/000114 dated Aug. 11, 2021; 7 pages.
International Search Report for PCT/IB2021/000117 dated Aug. 11, 2021; 7 pages.
Japanese Office Action for Application No. 2013-552885 dated Aug. 25, 2015.
Li, et al., "Medical pelvic migration of the lag screw in a short gamma nail after hip fracture fixation: a case report and review of

(56) References Cited

OTHER PUBLICATIONS the literature", Journal of Orthopaedic Surgery and Research, Aug. 2010, 5:62, pp. 1-7.
Partial Search Report including the Provisional Opinion for International Application No. PCT/IB2021/000114, dated Jun. 21, 2021, 10 pages.
Partial Search Report including the Provisional Opinion for International Application No. PCT/IB2021/000117, dated Jun. 21, 2021, 13 pages.
Synthes, "Titanium Trochanteric Fixation Nail System-Screw Option. For intramedullary fixation of proximal femur fractures.", Copyright date 2010, pp. 1-67.

* cited by examiner

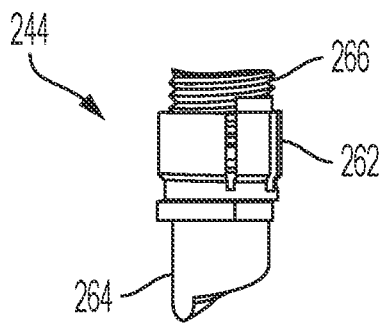
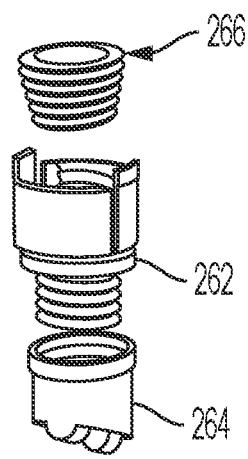
FIG. 7A FIG. 7B
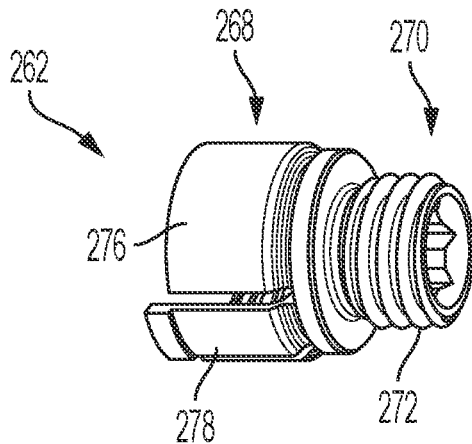
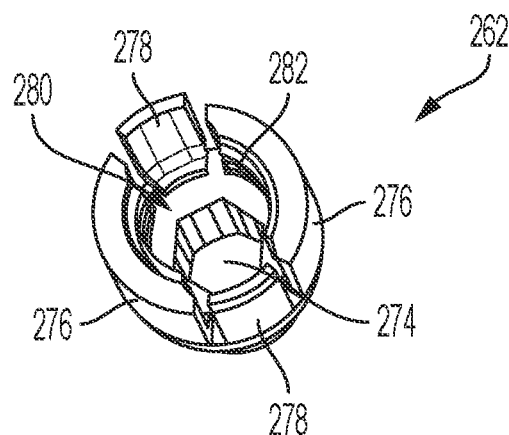
FIG. 8A FIG. 8B
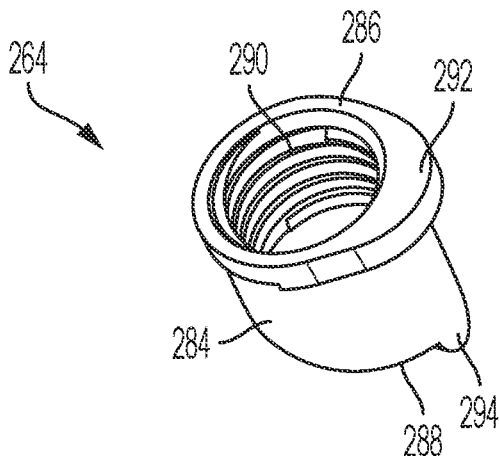
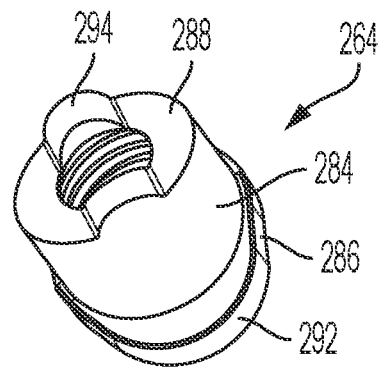
FIG. 9A FIG. 9B

SET SCREW FOR FEMORAL NAIL

CROSS-REFERENCE TO RELATED APPLICATIONS

The present application is a national phase entry under 35 U.S.C. § 371 of International Application No. PCT/IB2021/000114 filed Mar. 3, 2021, which claims priority from U.S. Provisional Application No. 62/985,981, filed Mar. 6, 2020, the disclosures of which are each hereby incorporated by reference herein.

BACKGROUND OF THE INVENTION

The present invention relates generally to an intramedullary intertrochanteric device for internal fixation of a fractured long bone.

Femoral fractures often occur in the femoral neck and trochanteric regions. Such fractures are commonly treated with intramedullary intertrochanteric fracture fixation devices. Examples of these devices are disclosed in U.S. Pat. Nos. 5,176,681, 5,454,813 and 9,072,552, the disclosures of which are each incorporated herein by reference in their entireties. Intramedullary intertrochanteric fracture fixation devices of this type include an intramedullary rod (sometimes referred to as an intramedullary nail or femoral nail) having an angulated opening to receive a neck screw such as a lag screw. The neck screw is designed to transfer the load from the femoral head into the shaft of the femoral nail while bridging the fracture line such that the fractured bone portions are compressed together and stabilized during osteogenesis.

Intramedullary nails are intended to be inserted into the medullary canal of the femur over a guidewire. The guidewire aids in retaining proper placement of the fractured bone portions while the nail is inserted into the medullary canal of the bone. Once the intramedullary nail has reached its intended position within the medullary canal, the guidewire may be removed, thus allowing the neck screw to be inserted into the angulated opening of the femoral nail and into intertrochanteric bone. A fastener such as a set screw is then inserted through an axial bore defined in a proximal portion of the intramedullary nail to fasten the neck screw to the nail.

Postoperative rotational movement of the fractured bone fragments can lead to complications such as shortening of the neck of the femur, which may result in reduced physical function. It is therefore desirable to compress the fracture site intra-operatively and then stabilize the bone portions to minimize their postoperative rotational movement during healing of the bone. Nevertheless, it is sometimes advantageous to allow for limited axial sliding of the neck screw relative to the intramedullary nail to account for load shifting, for example, when the weight of a patient is applied to his or her hip.

Traditional intramedullary intertrochanteric fracture fixation devices are not without drawbacks. For example, conventional set screws occlude the axial bore such that the set screw cannot be inserted into the intramedullary nail until after the intramedullary nail has been implanted in the medullary canal of the bone and the guidewire has been removed. This is problematic because fastening the set screw to the neck screw can be a time consuming process when performed intraoperatively as soft tissue often overlaps the proximal end of the axial bore. Reamed bone fragments disposed within the axial bore further exacerbates the already difficult task of engaging the threading of the set screw with corresponding threading in the femoral nail. Moreover, improper threading of the set screw can damage the set screw or the intramedullary nail, making the set screw susceptible to backing out, which can lead to postoperative rotation of the fractured bone portions.

Therefore, there is a need for an improved set screw assembly that can be easily fastened to the neck screw and that ensures postoperative rotational stability of the fractured bone portions.

BRIEF SUMMARY OF THE INVENTION

In accordance with a first aspect of the present invention, a cannulated set screw for use in an inintramedullary intertrochanteric fracture fixation device is provided. The cannulated set screw allows a user to fasten the set screw to corresponding threading of the femoral nail pre-operatively, thereby reducing error and operation time. The set screw includes a first member including a proximal portion and a distal portion, the proximal portion including at least one flange being moveable in a radial direction between an unlocked condition and a locked condition, the distal portion including a threading; and a second member including a sidewall extending between a proximal end and a distal end, the sidewall defining an interior surface having a threading for threadably mating the distal portion of the first member to the second member, the second member further including an extension configured to extend into the angulated opening to engage the neck screw and a lateral flange sized and configured to sit within a slot defined in an interior surface of the intramedullary nail to prevent rotational movement of the neck screw in the angulated opening.

In accordance with another aspect off the invention, the set screw includes a first member including a proximal portion and a distal portion, the proximal portion including a plurality of flanges being moveable in a radial direction between an unlocked condition and a locked condition, the plurality of flanges being annularly spaced from one another to define a first cavity; a second member including a sidewall extending between a proximal end and a distal end, the sidewall defining a second cavity for receiving the distal portion of the first member, the second member further including an extension configured to extend into the angulated opening to engage the neck screw and a lateral flange sized and configured to sit within a slot defined in an interior surface of the intramedullary nail; and a third member sized and configured to be inserted into the first cavity to transition the plurality of flanges from the unlocked condition to the locked condition.

In yet another aspect of the invention, an intramedullary intertrochanteric fracture fixation device is provided. The device includes an intramedullary nail having a proximal portion and a distal portion, the nail defining an angulated opening in the proximal portion and an axial bore extending through a proximal end of the nail and into the angulated opening, the proximal portion of the nail further having a set screw receiving cavity defined by an upper stop, a lower stop and a sidewall, the sidewall of the set screw receiving cavity defining a slot; a neck screw extending through the angulated opening, the neck screw including an exterior surface extending along a length between a proximal end and a distal end, the exterior surface defining a groove; and a set screw disposed within the intramedullary nail and selectively moveable into the set screw receiving cavity, the set screw including a first member removably coupleable to a second member, the first member having a flange engageable with the upper stop to limit proximal movement of the set screw, the second member including a flange engageable with the lower stop to limit distal movement of the set screw, the second member being extendable through the angulated opening and into the groove of the neck screw, wherein the flange of the second member is positionable within the groove to prevent rotational movement of the neck screw in the angulated opening.

BRIEF DESCRIPTION OF THE DRAWINGS

FIG. 7A is a side elevation view depicting the set screw assembly of FIG. 6A in an assembled state.

FIG. 7B is an exploded view of the set screw assembly of FIG. 7A.

FIG. 8A is front oriented perspective view of a first locking member of the set screw assembly shown in FIGS. 7A and 7B.

FIG. 8B is a top oriented perspective view of the first locking member shown in FIG. 8A.

FIG. 9A is a top oriented perspective view of a second locking member of the set screw assembly shown in FIGS. 7A and 7B.

FIG. 9B is a bottom oriented perspective view of the second locking member shown in FIG. 9A.

DETAILED DESCRIPTION

As used herein, when referring to the femur or the intramedullary nail when implanted into the medullary canal of a patient, the term "proximal" means closer to the heart and the term "distal" means more distant from the heart. The term "anterior" means towards the front part of the body or the face and the term "posterior" means towards the back of the body. The term "medial" means toward the midline of the body and the term "lateral" means away from the midline of the body. When referring to the neck screw, the term "rear" means closer to the user, whereas the term "front" means further from the user.

Throughout this description, a fracture refers to a femoral neck fracture, however, the devices described hereinafter can be used to fixate associated fractures of the femoral shaft as well as factures in other long bones, for example, the tibia or the humorous, whether the fracture be naturally occurring or surgeon-induced.

Figure 1:
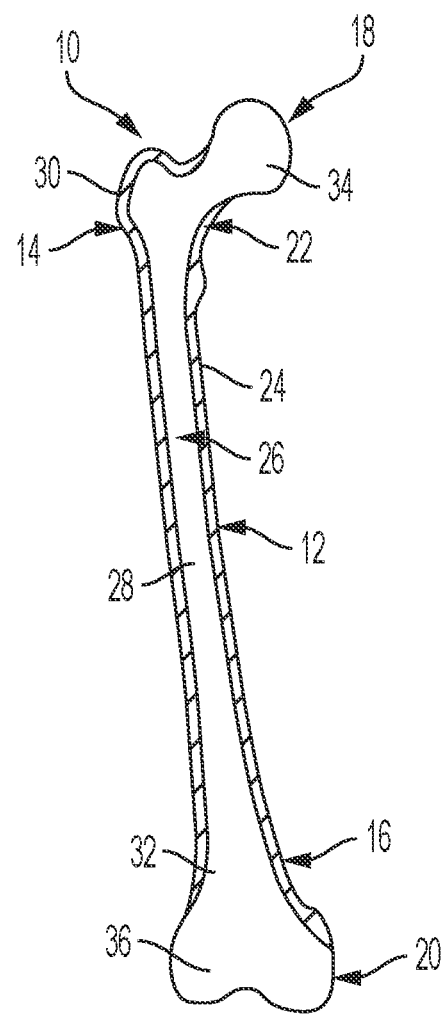
FIG. 1 is a cross section view of a femur.

FIG. 1 illustrates a femur 10 and its six anatomical regions: a diaphysis or midshaft 12, proximal metaphysis 14, distal metaphysis 16, proximal epiphysis or head 18, distal epiphysis 20, and a femoral neck 22. The femur 10 includes a hard cortex 24 and a medullary cavity 26. The medullary cavity 26 includes a medullary canal 28 which runs through the center of shaft 12, the proximal and distal metaphyseal areas 30 and 32, and the proximal and distal epiphyseal areas 34 and 36.

Figure 2:
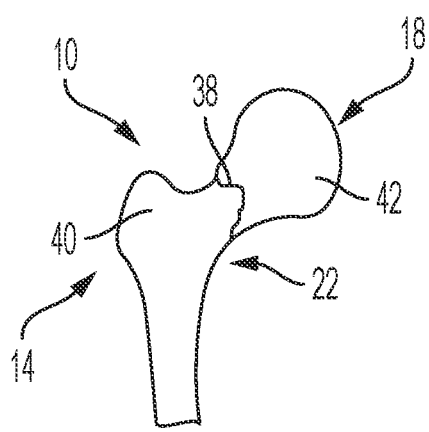
FIG. 2 is an anterior-posterior elevation view of a proximal femur having a femoral neck fracture.

FIG. 2 is an anterior-posterior view of a proximal portion of femur 10 having a fracture 38 extending along femoral neck 22. Fracture 38 separates the proximal femur into a first bone portion 40 adjacent the proximal metaphysis 14 and a second bone portion 42 adjacent the proximal epiphysis or head 18. Fracture 38 is an exemplary illustration of an unstable, extra-articular fracture, i.e., the fracture is located outside of a joint. This type of fracture, if not treated, can lead to long-term complications including comminution (i.e., pulverization of the bone), which may result in shortening of femoral neck 22 and severe pain.

Figure 3:
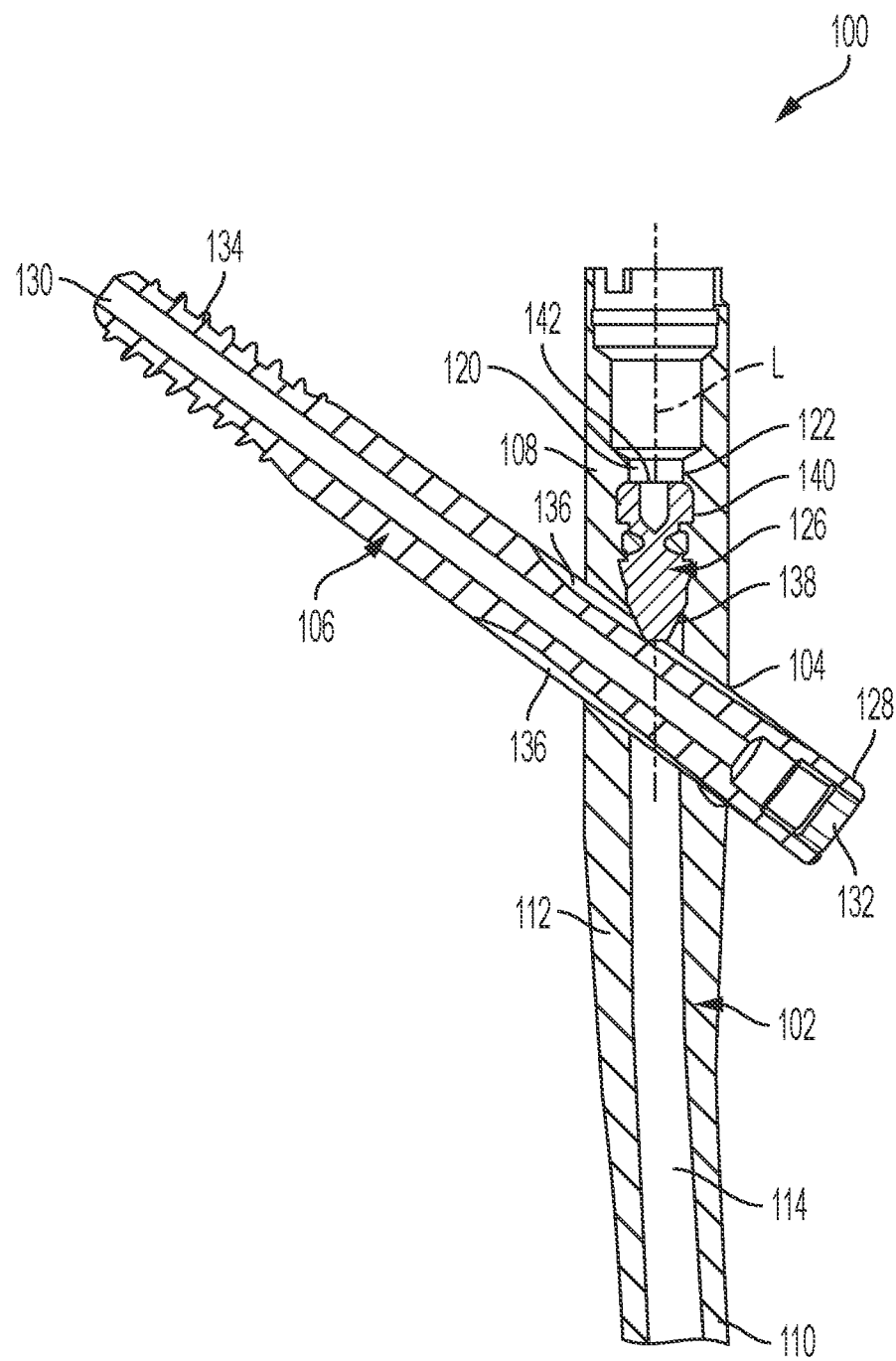
FIG. 3 is cross section view of a known intramedullary intertrochanteric fracture fixation device including an intramedullary nail, a neck screw and a set screw.

Referring to FIG. 3, a known intramedullary intertrochanteric fracture fixation device 100 is shown for compressing first and second bone portions, and for maintaining rotationally stability between the first and second bone portions during healing of fracture 38. Intramedullary intertrochanteric fracture fixation device 100 generally includes an intramedullary nail 102 having an angulated opening 104 extending through the nail in the lateral to medial direction, a neck screw 106 that is insertable through the angulated opening for compressing the fractured bone portions together and a set screw 126 for rotationally stabilizing the neck screw within the angulated opening.

Figure 4:
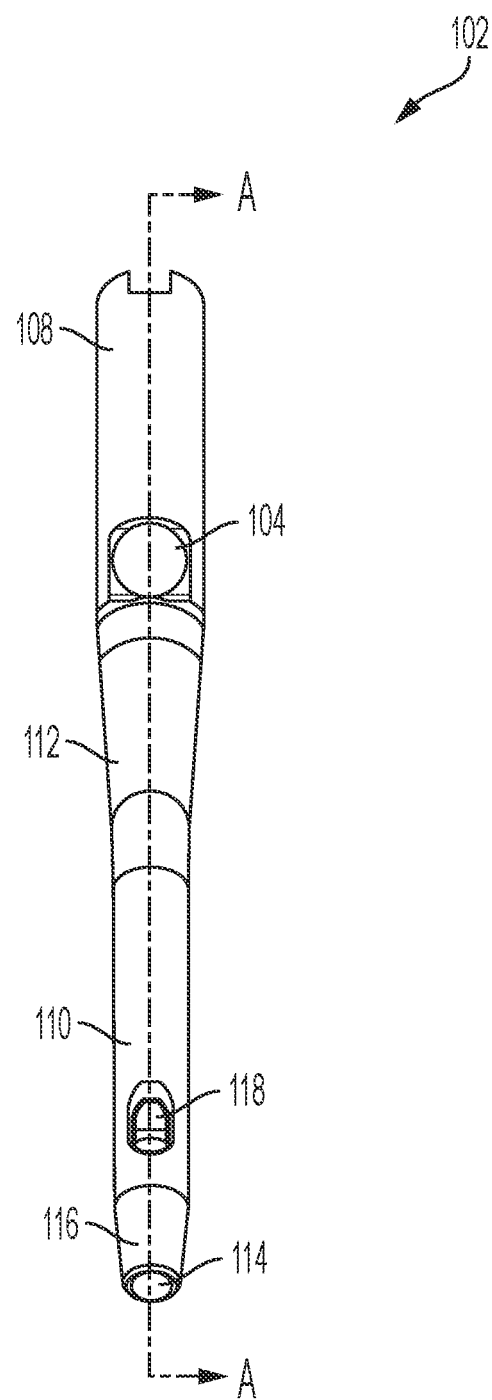
FIG. 4 is a lateral side perspective view of the intramedullary nail shown in FIG. 3.

Referring to FIG. 4, intramedullary nail 102 includes a rod-shaped body having a proximal portion 108, a distal portion 110 and an intermediate portion 112 located between and connecting the proximal and distal portions. The rod-shaped body of intramedullary nail 102 is anatomically shaped to allow the intramedullary nail to be inserted into the medullary canal 28 of femur 10 (shown in FIG. 1). For this reason, intermediate portion 112 is bent and tapered in the proximal to distal direction.

The rod-shaped body of intramedullary nail 102 is cannulated and defines a channel 114 that is configured to receive a surgical wire (not shown), such as a K-wire wire, for guiding the intramedullary nail into a proper position within the medullary canal 28 of the femur 10. Intramedullary nail 102 has a substantially circular cross-section over its entire length such that proximal portion 108 and distal portion 110 are substantially cylindrical. The proximal portion 108 of intramedullary nail 102 has a diameter sufficient to accommodate angulated bore 104. The distal portion 110 of intramedullary nail 102 has a diameter that is smaller than the diameter of proximal portion 108, and that is anatomically shaped to the medullary canal 28 of femur 10 to facilitate the insertion of the distal portion of the intramedullary nail into the medullary canal of the femur. For the same reason, the distal portion 110 of intramedullary nail 102 has a conical tip 116 at its distal end. The distal portion 110 of intramedullary nail 102 also defines an aperture 118 configured to receive a bone fastener such as a locking screw for fastening the intramedullary nail to the shaft 12 of femur 10.

Figure 5:
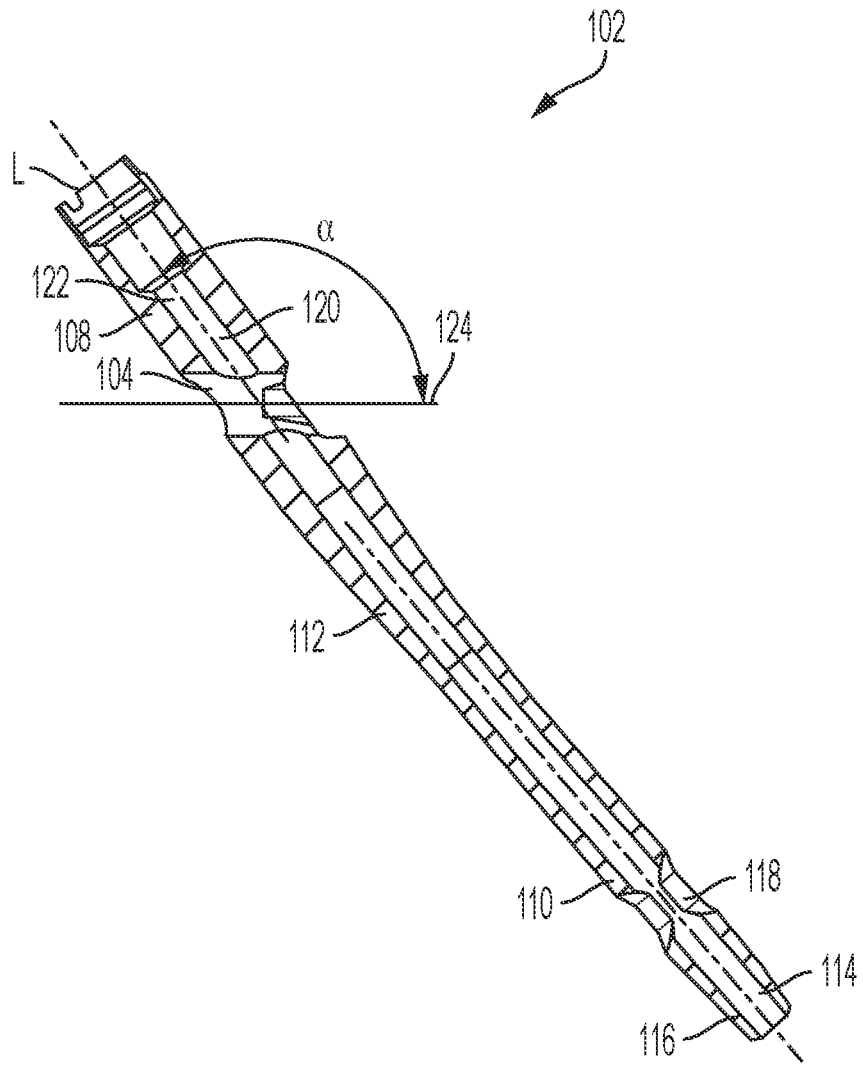
FIG. 5 is a cross-section view of the intramedullary nail taken along line A-A of FIG. 4.

As shown in FIG. 5, the proximal portion 108 of intramedullary nail 102 has an axial bore 122 that extends along a longitudinal axis L of the proximal portion and between the proximal end of the nail and angulated opening 104. Axial bore 122 defines a compartment 120 in the proximal portion 108 of intramedullary nail 102. Compartment 120 may include internal threading (not shown) configured to mate with corresponding threading provided on set screw 126 (shown in FIG. 3).

Angulated opening 104 defines a bore axis 124 that is transversely angled with respect to the longitudinal axis L of proximal portion 108 such that the bore axis of the angulated opening has an oblique extension relative to an axial extension of the proximal portion. In other words, bore axis 124 of angulated opening 104 is oriented obliquely with respect to the longitudinal axis L of the proximal portion 108. Thus, the bore axis 124 of angulated opening 104 is inclined at an angle α with respect to the longitudinal axis L of the proximal portion 108. Angle α, for example, may be between approximately 90° and approximately 140°.

Returning to FIG. 3, neck screw 106 extends through angulated opening 104 in a lateral to medial direction. As will be explained in more detail below, neck screw 106 is coupled to intramedullary nail 102, via set screw 126, in a manner that prevents the neck screw from rotating in angulated opening 104 and that allows the neck screw to limitedly slide along the bore axis 124 to account for load shifting.

Neck screw 106 may be a lag screw extending along a length defined between a rear end 128 and a front end 130. The rear end 128 of neck screw 106 includes a recess 132, for example, a hexalobular internal driving feature for receiving a tool tip such as a screw driver or a wrench. The front portion adjacent the front end 130 of neck screw 106 includes a thread 134, such as a coarse thread, for anchoring the neck screw into intertrochanteric bone. Neck screw 106 further includes grooves 136 defined in the peripheral surface of the neck screw. Grooves 136 extending in a direction generally parallel to the longitudinal axis of neck screw 106. For example, neck screw 106 may include four grooves 136 circumferentially spaced about the peripheral surface of the neck screw at intervals of 90°. Each groove 136 defines a ramp having a shallow end and a deep end. The rising ramp extends from the rear portion of neck screw 106 toward the front portion of the neck screw. Because the longitudinal axis of neck screw 106 is substantially coaxial with the bore axis 124 of angulated opening 104, the neck screw is configured to transfer loads placed on the femoral head to the intramedullary nail 102, and at the same time, bridge the fracture 38 and compress bone portions 40, 42 together.

Set screw 126 includes an engagement member 138 and a drive member 140 connected to the engagement member. The drive member 140 of set screw 126 includes an external thread configured to threadably mate with corresponding internal threading provided in axial bore 122 and/or compartment 120. The drive member 140 of set screw 126 defines a recess 142, such as a hexalobular internal driving feature for receiving a tool (e.g., a screw driver) and selectively advancing the set screw (the combination of the driving member and the engagement member which are connected together) within the axial bore 122 of proximal portion 108. For example, using the driving tool, set screw 126 may be advanced distally within the axial bore 122 of proximal portion 108 by rotating the set screw in a first direction (e.g., clockwise). Set screw 126 may alternatively be retracted in the proximal direction within the axial bore 122 by rotating the set screw in a second direction opposite to the first direction (e.g., counterclockwise).

The engagement member 138 of set screw 126 may be a cylindrical bolt, pin or protrusion configured to be positioned within the grooves 136 of neck screw 106. When set screw 126 is axially advanced to a position in which groove 136 receives engagement member 138, rotational movement of the neck screw within the angulated opening 104 of intramedullary nail 102 is prevented.

When engagement member 138 is initially advanced in the distal direction and into groove 136, the engagement member exerts little to no force on neck screw 106. While the low force is sufficient in preventing neck screw 106 from rotating, the low force will permit movement of the neck screw along the axis 124 of angulated opening 104 relative to intramedullary nail 102. The sliding or axial movement of neck screw 106 will cause a change in force (typically an increase) due to the depth profile of the lateral and medial ramps of grooves 136. If the surgeon desires to limit axial sliding of neck screw 106 based upon specific consideration of a particular surgery, the surgeon may turn driving member 140 clockwise and tighten set screw 126 against neck screw 106 to increase the force and reduce or eliminate axial sliding of the neck screw. Alternatively, should the surgeon desire to increase axial sliding of neck screw 106, the surgeon may loosen set screw 126.

The present invention provides an intramedullary intertrochanteric fracture fixation device and various set screw assemblies for use with the fixation device. Each one of the set screw assemblies described hereinafter is cannulated and thus overcomes the drawbacks associated with set screw 126, namely the difficulties associated with intraoperative assembly. Because the set screw assemblies of the present invention are cannulated, the set screw assemblies can be pre-operatively assembled within the intramedullary nail and configured to receive a guidewire while disposed within the nail. That is, during operation, a surgeon may insert a guidewire through the cannula of the set screw assembly and guide the nail into position within the medullary canal of the patient. As used herein, the term "pre-operatively assembled" means that the set screw is assembled within the nail by the manufacturer before the fixation device is shipped, or alternatively, that the set screw assembly is assembled within the nail by a user before the nail is implanted into the medullary canal of a patient.

Each one of the set screw assemblies set forth below may be used with an intramedullary nail that is similar to intramedullary nail 102 and a neck screw that is similar to neck screw 106. Thus, specific features of the intramedullary nails and neck screws of the present invention are not described in detail in each embodiment unless the features are emphasized or unless the features are different than the features previously described with respect to intramedullary nail 102 and neck screw 106. Instead, when like features are mentioned, the features are renumbered with sequential 100 series numerals. For example, in describing the various embodiments of the set screw assemblies, the intramedullary nail will be referenced as intramedullary nail 202, 302, 402. Similarly, the neck screw will be referenced as neck screw 206, 306, 406.

Figure 6A:
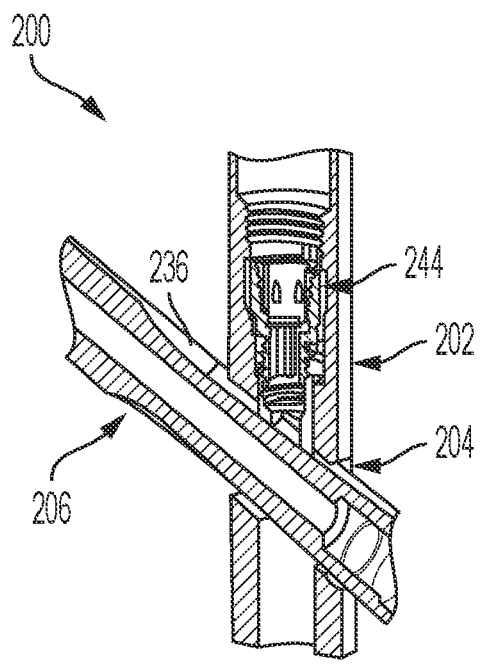
FIG. 6A is a partial cross section view of an intramedullary intertrochanteric fracture fixation device including an intramedullary nail, a neck screw and a set screw assembly in accordance with an embodiment of the present invention.

FIG. 6A illustrates an intramedullary intertrochanteric fracture fixation device 200 in accordance with an embodiment of the present invention. Fixation device 200 includes an intramedullary nail 202 having an angulated opening 204 extending through the nail in the lateral to medial direction, a neck screw 206 insertable through the angulated opening and a set screw assembly 244 for securing the neck screw to the nail. When implanted into the femur 10 of a patient, fixation device 200 is adapted to compress first bone portion 40 and second bone portion 42 together, and prevent post-operative relative rotation of the first and second bone portions during healing of fracture 38.

Figure 6B:
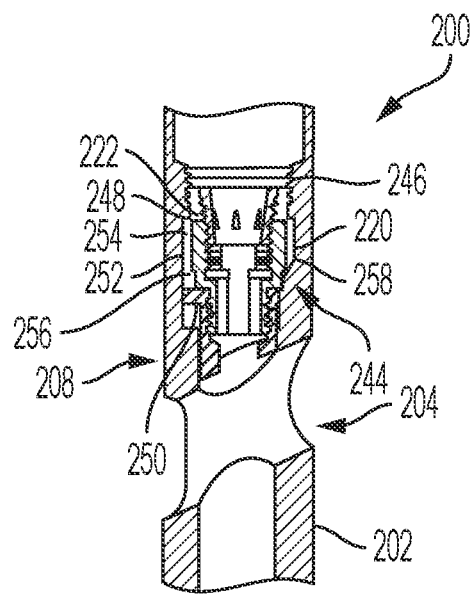
FIG. 6B is a cross section view of the intramedullary nail and the set screw assembly of FIG. 6A and depicts the set screw assembly being pre-operatively assembled within the intramedullary nail.
Figure 6C:
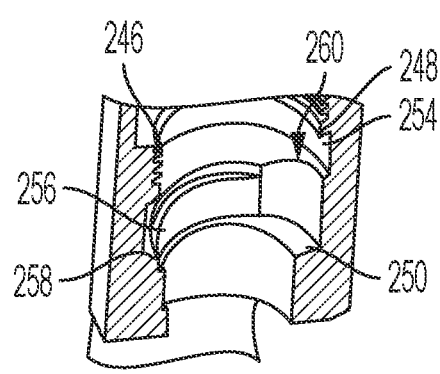
FIG. 6C is a perspective view of a proximal portion of the intramedullary nail shown in FIG. 6A.

FIG. 6B is a cross section view of set screw assembly 244 pre-operatively assembled within a proximal portion 208 of intramedullary nail 202. Intramedullary nail 202 defines an axial bore 222 that extends along a longitudinal axis of the nail, and between the proximal end of the nail and angulated opening 204. Axial bore 222 includes internal threading 246 and a compartment 220 located between the internal threading and angulated opening 204. Compartment 220 is adapted to receive and retain set screw assembly 244 and is defined by an upper ledge 248 for limiting proximal movement of the set screw assembly, a lower ledge 250 for limiting distal movement of the set screw assembly and a sidewall 252. Compartment 220 includes an upper portion 254 located adjacent to upper ledge 248, a lower portion 256 located adjacent to lower ledge 250 and an intermediate portion 258 located between the upper and lower portions. Intermediate portion 258 may taper inwardly from upper portion 254 to lower portion 256 such that the upper portion of the compartment has a greater diameter than the lower portion of the compartment. With specific reference to FIG. 6C, a longitudinally extending slot 260 is defined in the sidewall 252 of compartment 220. In some embodiments, slot 260 may extend between lower ledge 250 and the intermediate portion 258 of compartment 220.

Figure 6D:
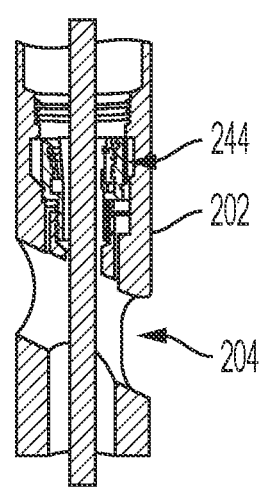
FIG. 6D is a cross section view depicting a guidewire extending through the set screw assembly and the intramedullary nail shown in FIG. 6B.

Set screw assembly 244, as illustrated in FIGS. 7A and 7B, includes a first member 262, a second member 264 and a third member 266. Each of the first, second and third members are cannulated such that when the members are coupled together and pre-operatively assembled within intramedullary nail 202, the set screw assembly 244 is configured to receive a guidewire as shown in FIG. 6D.

Referring now to FIGS. 8A and 8B, first member 262 includes a proximal portion 268 that is adapted to receive third member 266, and a distal portion 270 having threading 272 about its external surface for threadably coupling the first and second members together. With specific reference to FIG. 8B, a lumen 274 extends through distal portion 270. Lumen 274 may define a hexalobular internal driving feature adapted to receive a tool tip, such as a screw driver or a hex key, for rotating first member 262 in a first direction and threading the first member into second member 264, or alternatively, rotating the first member in a second direction and unthreading the first member from the second member.

The proximal portion 268 of first member 262 includes a sidewall 276 and a plurality of vertically extending flanges 278. The combination of the sidewall 276 and vertically extending flanges 278 circumscribe and define an internal receiving space 280 configured to receive third member 266. An interior surface of sidewall 276 may include threading 282.

Flanges 278 are adapted to flex radially outward as a force is applied on an interior surface of the flange, for example, when third member 266 is forced into receiving space 280. In one embodiment, flanges 278 may include thickened proximal ends for engaging the sidewall 252 of compartment 220, and for contacting the upper stop 248 of the compartment. Although FIGS. 8A and 8B illustrate the proximal portion 268 of first member 262 as having two diametrically opposed flanges 278, it will be understood that the first member may alternatively have one flange, or any number of flanges greater than two. An exterior surface of the proximal portion 268 of first member 262 may include a taper at a location adjacent to the distal portion 270 of the first member that corresponds to the taper of the intermediate portion 258 of compartment 220. In one embodiment, the exterior surface of the sidewall 276 of proximal portion 268 may include a threading (not shown) for threadably mating set screw assembly 244 to the internal threading 246 provided within the proximal portion 208 of intramedullary nail 202.

With reference to FIGS. 9A and 9B, second member 264 includes a cannulated body 284 having a proximal end 286 and a distal end 288. An internal surface of cannulated body 284 includes a threading 290 that corresponds to threading 272 provided on the distal portion 270 of first member 262 such that the distal portion of the first member can be threadably secured within the body of the second number.

The proximal end 286 of second member 264 includes a laterally extending flange 292. As illustrated, the laterally extending flange 292 may have arcuate shape that is sized to be positioned within longitudinal slot 260 for preventing rotational movement of the second member within compartment 220, and a bottom surface for contacting lower ledge 250 for limiting distal movement of the second member. As shown in FIGS. 9A and 9B, one or more extensions 294 may protrude from the distal end 288 of second member 264. Extension 294 is sized and shaped to extend into the angulated opening 204 and into one of the grooves 236 of neck screw 206 when set screw assembly 244 is disposed within intramedullary nail 202. The distal end 288 of second member 264 may be traversely angled relative to the proximal end 286 of the second member such that when set screw assembly 244 is disposed within compartment 220, only the extension 294 protrudes into angulated opening 204.

Figure 10:
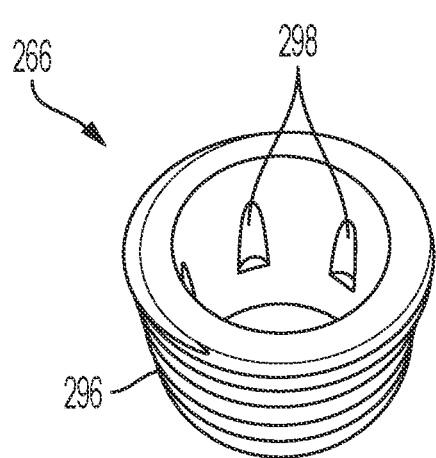
FIG. 10 is top oriented perspective view of a frustoconical spreading member of the set screw assembly shown in FIGS. 7A and 7B.

Referring to FIG. 10, third member 266 is cannulated and is generally frustoconical in shape. That is, the proximal end of third member 266 has a greater diameter than the distal end of the third member. In one embodiment, as shown in FIG. 10, an exterior surface of third member 266 includes a threading 296 that corresponds to the threading 282 provided on the interior sidewall 276 of first member 262 such that the third member may be threaded into the receiving cavity 280 of the first member. A plurality of recesses 298 may be circumferentially disposed about an interior sidewall of third member 266 for receiving the tip of a driving tool and rotating the third member to thread the third member into the receiving cavity 280 of first member 262, or alternatively, rotating the third member in an opposite direction to retract the third member from the receiving cavity of the first member.

Figure 11:
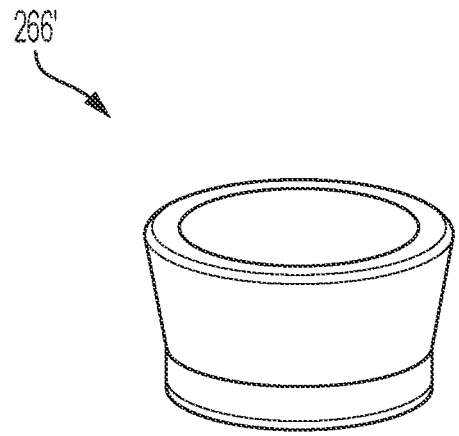
FIG. 11 is top oriented perspective view of an alternate frustoconical spreading member.

Alternate third member 266', shown in FIG. 11, does not include external threading. Instead, the external surface of third member 266' is flat such that the alternate third member may slide into the receiving cavity of the first member. It will be appreciated that in the alternate embodiment, the inner sidewall of the receiving cavity need not include threading. Moreover, alternate third member 266' may include one or more recesses (not shown) configured to receive a driving tool for pushing or otherwise driving the alternate third member into the receiving cavity of the first member.

Use of intramedullary intertrochanteric fracture fixation device 200 for healing fracture 38 will now be described with reference to FIGS. 6A, 6B, 6D, 7A and 7B. To assemble set screw assembly 244, the distal portion 270 of first member 262 is threaded into second member 264 until the proximal portion 268 of the first member contacts the upper surface of the lateral flange 292 of the second member. The third member 266 is then partially threaded or otherwise inserted into the receiving cavity 280 of first member 262. At this stage, as illustrated in FIG. 7A, the proximal end of the third member remains outside of the receiving cavity 280 of first member 262 such that the vertical flanges 278 of the first member are in an unbiased condition (e.g., substantially vertically oriented).

Assembled set screw assembly 244 may then be preoperatively assembled within the proximal portion 208 of intramedullary nail 202 such that the set screw assembly is engaged with the internal threading 246 of the intramedullary nail or otherwise positioned proximal to compartment 220. As shown in FIG. 6D, a surgeon may then insert a guidewire through the cannulated set screw assembly 244 and use the guidewire in a conventional manner to advance the intramedullary nail 202 into position within the medullary canal 28 of the patient. After intramedullary nail 202 has been positioned within the medullary canal 28 of femur 10, the surgeon may remove the guidewire and insert neck screw 206 through the angulated opening 204 of the intramedullary nail in order to compress the fractured bone portions together.

Set screw assembly 244 may then be threaded or otherwise pushed into compartment 220 as shown in FIG. 6B (neck screw not shown for clarity) and rotated until lateral flange 292 is positioned within slot 260. Once slot 260 has received lateral flange 292, second member 264 will be prevented from rotating within compartment 220. Set screw assembly 244 may then be further driven in the distal direction along longitudinal axis L until the underside of lateral flange 292 engages the lower stop 250 of compartment 220 and the extension 294 of second member 264 extends into the groove 136 of neck screw 206, thereby preventing the neck screw from rotating about bore axis 124 and relative to the extensions of the set screw assembly. Neck screw 206 is thus effectively prevented from rotating within angulated opening 204.

After the surgeon has confirmed that neck screw 206 is appropriately positioned within the intertrochanteric bone, the surgeon may then insert a driving tool into the recesses 298 of third member 266, or into the recesses of third member 266', to drive the third member into the receiving cavity 280 of first member 262. As third member 266, or third member 266', is driven into the receiving cavity 280 of first member 262, the frustoconical shape of the third member forces the vertical flanges 278 of the first member to bias outwardly and toward the sidewall 252 of compartment 220. The biased flanges 278 of first member 262 will prevent set screw assembly 244 from backing out of compartment 220 even if a proximal force is applied to the set screw assembly. For example, due to the angulation of angulated opening 204 and the ramped surfaces of the grooves 236, axial movement of neck screw 206 results in a proximal force being applied to neck screw 206 and in some instances proximal movement of set screw assembly 244. However, the proximal movement of set screw assembly 244 will be limited by engagement between the vertical flanges 278 of first member 262 and the upper ledge 248 of compartment 220 as is further explained below.

The surgeon may optionally choose to limit the relative axial movement between neck screw 206 and intramedullary nail 202. In order to set this limit, the surgeon inserts a driving tool such as a hex key into the lumen 274 of the distal portion 270 of first member 262 and rotates the first member until the desired limit has been reached. Because the lateral flange 292 of second member 264 is positioned within slot 260 and the second member is prevented from rotating within compartment 220, rotation of the first member 262 will result in the threading or the unthreading of the first member from the second member and relative axial movement between the first and second members. Consequently, if the surgeon desires to decrease the relative axial movement between neck screw 206 and intramedullary nail 202, the surgeon may rotate the driving tool in a first direction (e.g., counter clockwise) causing the distal portion 270 of the first member 262 to unthread from the body 284 of second member 264 such that the first member moves in the proximal direction relative to the second member. Proximal movement of first member 262 relative to second member 264 will increase the overall length of set screw assembly 244 and decrease the distance between the proximal end of the vertical flanges 278 of the first member and the upper stop 248 of compartment 220. As a result, the permitted movement of neck screw 206 in an axial direction will be reduced, as even slight movement of the neck screw will result in proximal movement of set screw assembly 244 and engagement between the proximal end of the vertical flanges 278 and the upper stop 248 of compartment 220.

Once the vertical flanges 278 engage the upper stop 248 of compartment 220, further proximal movement of set screw assembly 244 will be prevented and the set screw assembly will apply a counter-force on neck screw 206, thereby prohibiting further axial movement of the neck screw. Accordingly, if the surgeon desires to prevent all axial sliding of neck screw 206, the surgeon may intraoperatively rotate first member 262 in the counter clockwise direction until the proximal end of the vertical flanges 278 engage the upper stop 248 of compartment 220. In contrast, if the surgeon desires to increase the amount of relative axial movement between neck screw 206 and intramedullary nail 202, the surgeon may rotate the driving tool in a second direction (e.g., clockwise). Clockwise rotation of first member 262 relative to the second member 264 will result in the distal portion 270 of the first member being threaded into the body 284 of the second member, thereby increasing the distance between the proximal end of the vertical flanges and the upper stop 248 of compartment 220. As a result, neck screw 206 will be permitted to slide relatively further in the axial direction before the vertical flanges 278 of first member 262 contact the upper stop 248 of compartment 220.

Figure 12:
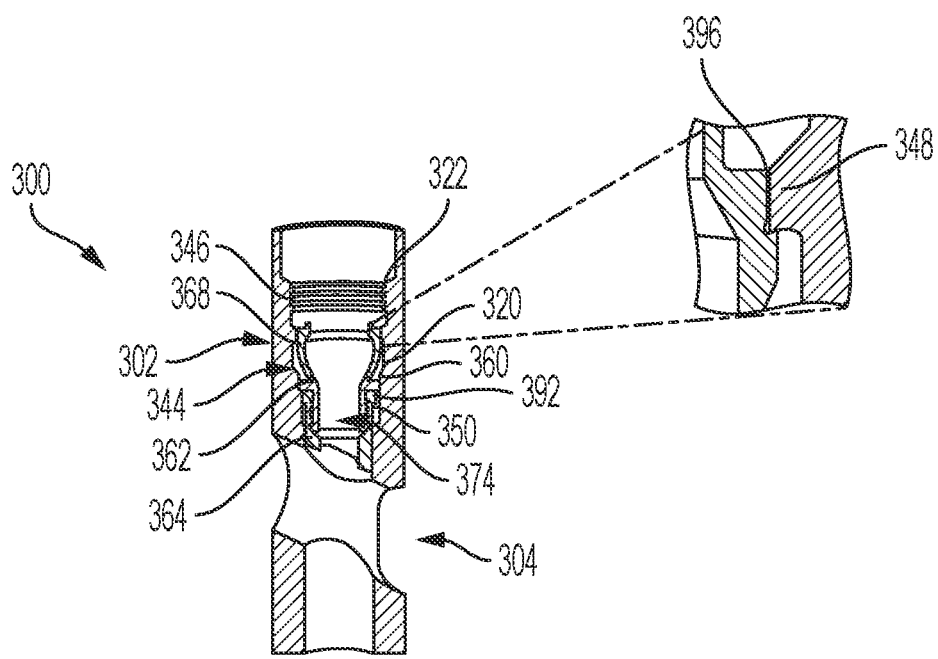
FIG. 12 is a partial cross-section view of a set screw assembly disposed within a proximal portion of a femoral nail in accordance with another embodiment of the present invention.
Figures 13A, 13B:
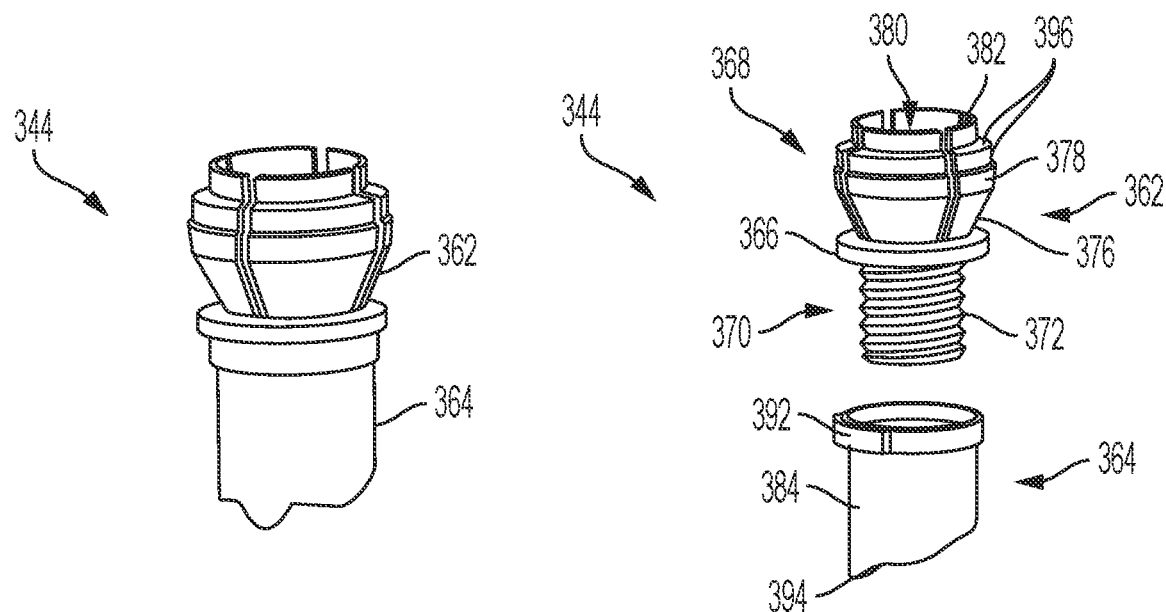
FIG. 13A is a side elevation view of the set screw assembly of FIG. 12 in an assembled state.
FIG. 13B is an exploded view of the set screw assembly of FIG. 13A.

FIGS. 12-13B illustrate a proximal portion of an intramedullary intertrochanteric fracture fixation device 300 in accordance with another embodiment of the invention. Fixation device 300 includes an intramedullary nail 302, a neck screw (not shown) and a set screw assembly 344. Although FIG. 12 does not illustrate a neck screw, it will be understood that fixation device 300 includes a neck screw similar to neck screw 206.

Set screw assembly 344 may be pre-operatively assembled within intramedullary nail 302 as shown in FIG. 12. Intramedullary nail 302 is substantially the same as previously described intramedullary nail 202. For this reason, intramedullary nail 302 is not described hereinafter in detail. Instead, where like features are mentioned, these features are referenced with corresponding 300 series numerals.

Referring to FIGS. 13A and 13B, set screw assembly 344 includes a cannulated first member 362 and a cannulated second member 364 such that when the first and second members are coupled together and pre-operatively assembled within intramedullary nail 302, the set screw assembly is configured to receive a guidewire (not shown).

Second member 364 is substantially the same as previously described second member 264 (shown in FIGS. 9A and 9B). Accordingly, second member 364 is not described again in detail. Instead, where like features are recited, the like features are referenced using corresponding 300 series numerals.

First member 362 includes a proximal portion 368, a distal portion 370 and a ring-like intermediate portion 366 disposed between the proximal and distal portions. Distal portion 370 includes a threading 372 provided about an exterior surface of the distal portion for threadably coupling the first and second members together. Referring back to FIG. 12, distal portion 370 defines a lumen 374 adapted to receive a tool tip, such as a screw driver or a hex key, for rotating first member 362 in a first direction and threading the first member into second member 364, or alternatively, rotating the first member in a second direction and unthreading the first member from the second member.

The proximal portion 368 of first member 362, as illustrated in FIGS. 13A and 13B, includes a plurality of flexible flanges 378. Each one of the flanges 378 has an attached end 376 connected to the intermediate portion 366, a free end 382 opposite to the attached end and one or more step-like notches 396 provided between the attached end and the free end. The attached ends 376 of flanges 378 are connected to the intermediate portion 366 at a location adjacent to the circumferential edge of the intermediate portion such that the plurality of flanges circumscribes and defines an internal cavity 380. Although FIGS. 13A and 13B illustrate the proximal portion 368 of first member 362 as having four flanges 378, it will be understood that the first member may alternatively have two or three flanges, or any number of flanges greater than four.

Each one of the flanges 378 are spaced apart from adjacent flanges such that a gap 398 is formed therebetween allowing the flanges 378 flex radially inward as a force is applied to the exterior surface of the flanges. The step-like notches 396 are sized and configured to receive the upper ledge 348 of compartment 320. The flexible flanges 378 may be tapered radially outwardly from the attached end 376 toward the step-like notches 396 such that the proximal portion 368 of first member 362 is generally bulbous shaped.

Use of intramedullary intertrochanteric fracture fixation device 300 for healing fracture 38 will now be described with reference to FIGS. 12-13B. To assemble set screw assembly 344, the distal portion 370 of first member 362 is threaded into the body 384 of second member 364 until the intermediate portion 366 of the first member contacts the lateral flange 392 of the second member.

Assembled set screw assembly 344 may then be inserted through the proximal end of intramedullary nail 302 and pre-operatively positioned within the axial bore 322 of the nail such that the set screw assembly is engaged with the internal threading 346 of the intramedullary nail, or otherwise positioned proximal to compartment 320. A surgeon may then insert a guidewire through the cannulated set screw assembly 344 and use the guidewire in a conventional manner to advance the intramedullary nail 302 into position within the medullary canal 28 of the patient. After intramedullary nail 302 has been positioned within the medullary canal 28 of femur 10, the surgeon may remove the guidewire and insert a neck screw through the angulated opening 304 of the intramedullary nail in order to compress the fractured bone portions together.

Set screw assembly 344 may then be driven distally into compartment 320 as shown in FIG. 12 (neck screw not shown for clarity) and rotated until the lateral flange 392 of second member 364 is positioned within the longitudinal slot 360 of the compartment. Once the longitudinal slot has received lateral flange 392, second member 364 is prevented from rotating within compartment 320. Set screw assembly 344 may then be further driven in the distal direction until the underside of the lateral flange 392 of second member 364 engages the lower stop 350 of compartment 320 and the extensions 394 of the second member extend into a groove of the neck screw. As a result, the neck screw is prevented from rotating within angulated opening 304.

As the proximal portion 368 of first member 362 is driven distally into compartment 320, the inner edge of the upper ledge 348 contacts and applies a compression force to the outwardly tapered surface of flanges 378. The compression force causes the flanges to flex radially inward toward the interior cavity 380 of first member 362. Gaps 398 aid in the flexing of flanges 378. Once the outwardly tapered surface of flanges 378 has been passed through the upper ledge 348 of compartment 320, the flanges radially expand to their natural condition and the step-like notches 396 engage the upper ledge of the compartment as shown in FIG. 12. The engagement between notches 396 and the upper ledge 348 of compartment 320 prevents set screw assembly 344 from backing out of the compartment even when a proximal force is applied to the set screw assembly, for example, when the neck screw slides along angulated opening 304.

Set screw assembly 344 provides the surgeon the ability to limit relative axial movement between the neck screw assembly and the intramedullary nail 302. In order to intraoperatively set this limit, the surgeon may insert a driving tool such as a hex key into the lumen 374 of the distal portion 370 of first member 362 and rotate the first member independently and relative to second member 364. For example, if the surgeon desires to decrease the relative axial movement between the neck screw and intramedullary nail 302, the surgeon may rotate the driving tool in a first direction (e.g., counter clockwise) causing the second member 364 to unthread from the distal portion 370 of first member 362, and the extensions 394 of the second member 364 to move further into the grooves of the neck screw, thus reducing the distance that the neck screw is permitted to slide. On the other hand, if the surgeon desires to increase the amount of relative axial movement between the neck screw and the intramedullary nail, the surgeon may rotate the driving tool in a second direction (e.g., clockwise) causing the extensions 394 of the second member 364 to retract away from the neck screw, thus permitting the neck screw to slide relatively further in the axial direction.

Figure 14:
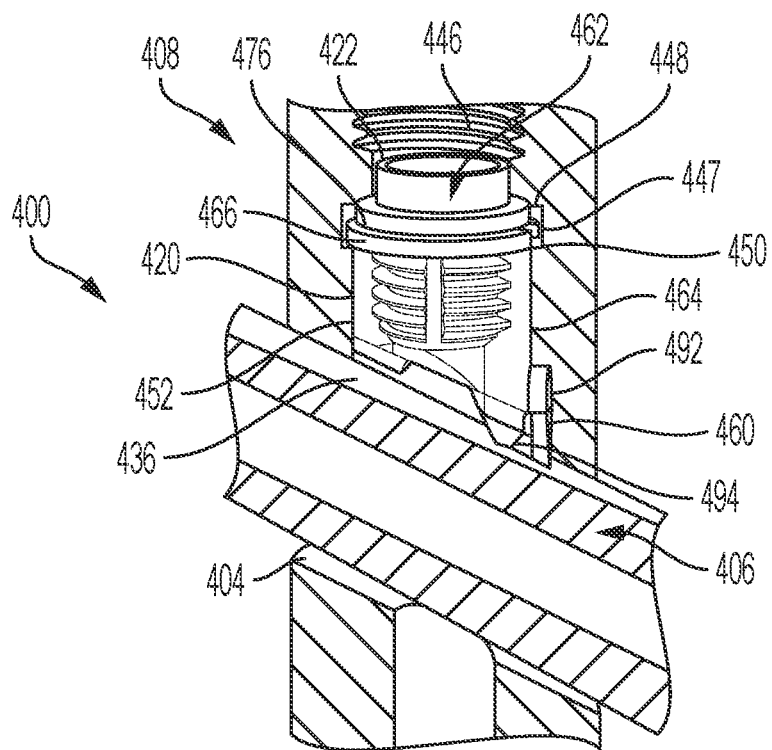
FIG. 14 is a partial cross section view of an intramedullary intertrochanteric fracture fixation device including an intramedullary nail, a neck screw and a set screw assembly in accordance with a yet another embodiment of the present invention and depicts the set screw assembly in a pre-operatively assemble state.
Figure 15A:
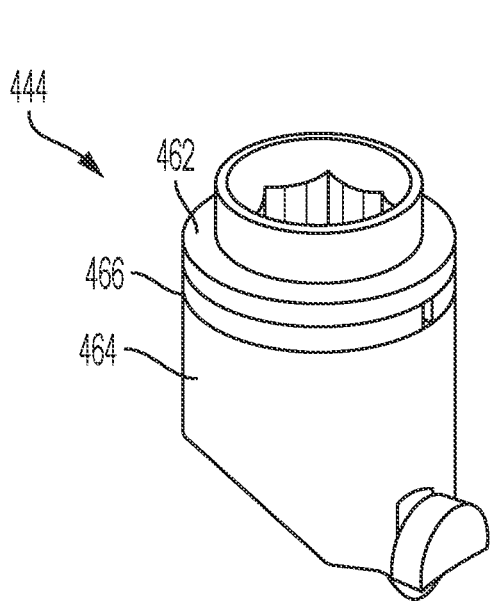
FIG. 15A is a perspective view of the set screw assembly of FIG. 14 in an assembled state.
Figure 15B:
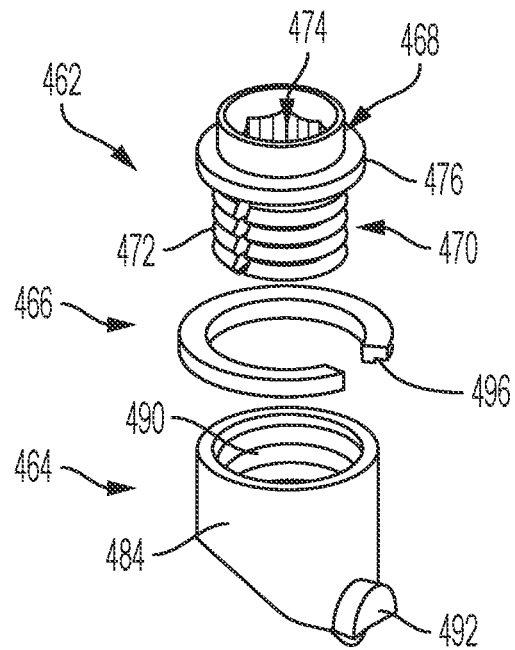
FIG. 15B is an exploded view of the set screw assembly of FIG. 15A.
Figure 16:
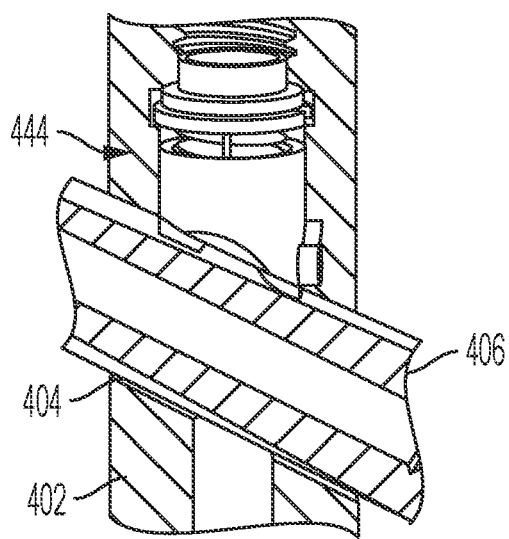
FIG. 16 is a partial cross section view of the intramedullary intertrochanteric fracture fixation device of FIG. 14 depicting the set screw assembly in a locked position.

FIGS. 14-16 illustrate a proximal portion of an intramedullary intertrochanteric fracture fixation device 400 in accordance with a further embodiment of the invention. Fixation device 400 includes an intramedullary nail 402 having an angulated opening 404 extending through the intramedullary nail in the lateral to medial direction, a neck screw 406 insertable through the angulated opening and a set screw assembly 444 for securing the neck screw to the nail. When implanted into the femur of a patient, fixation device 400 is adapted to compress first bone portion 40 and second bone portion 42 together, and prevent postoperative relative rotation of the first and second bone portions during healing of fracture 38.

FIG. 14 is a cross section view of set screw assembly 444 pre-operatively assembled within a proximal portion 408 of intramedullary nail 402. Intramedullary nail 402 defines an axial bore 422 extending along a longitudinal axis of the nail, and between the proximal end of the nail and angulated opening 404. Axial bore 422 includes internal threading 446 and a compartment 420 located between the internal threading and angulated opening 404. Compartment 420 is adapted to receive and retain set screw assembly 444 and is defined by an upper notch 447 having an upper ledge 448 and a lower ledge 450, a lower longitudinal slot 460 and a sidewall 452. Lower slot 460 is defined in the sidewall 452 of compartment 420 and may extend from a location adjacent angulated opening 404 toward the lower ledge 450 of upper notch 447.

Referring to FIG. 15A, set screw assembly 444 includes a first member 462, a second member 464 and a split ring 466. First member 462 and second member 464 are cannulated such that when the first and second members are coupled to split ring 466 and pre-operatively assembled within fixation device 400, the set screw assembly 444 is configured to receive a guidewire.

Referring now to FIG. 15B, first member 462 is a fastening member having a head or proximal portion 468, a threaded shaft or distal portion 470 and a neck 476 disposed between the head and the shaft. Shaft 470 includes threading 472 about its external surface for threadably coupling the first member 462 and the second member 464 together. Shaft 470 may optionally define one or more slits extending in a longitudinal direction along the shaft.

First member 462 also defines a lumen 274 that extends completely through the first member from the proximal end of head 468 to the distal end of shaft 470. Lumen 474 forms an internal driving feature, for example, a hexalobular driving feature adapted to receive a tool tip for rotating the first member in a first direction and threading the first member into second member 464, or alternatively, rotating the first member in a second direction and unthreading the first member from the second member.

Second member 464 is substantially the same as second member 264 and second member 364 except as discussed below Unlike second members 264, 364, second member 464 does not have a lateral flange extending from its proximal end. Instead, the proximal end 486 of second member 464 defines a rim for receiving split ring 466. Furthermore, second member 464 includes a protrusion 492 that extends in a lateral direction from the body 284 of the second member and preferably from a location adjacent to the distal end 488 of the second member. The protrusion 492 is sized and configured to be received in the slot 460 of compartment 420.

Split ring 266 may be formed from a compliant material such that the split ring is capable of radial compression and radial expansion. Split ring 266 is sized and shaped to be wedged between the neck 476 of first member 462 and the rim of the second member 464. Furthermore, split ring 266 may define a notch 496 that extends about the circumference of the split ring. The notch 496 of split ring 466 is complimentarily sized and shaped to the rim of second member 464 such that the split ring is designed to be seated on the rim of the second member.

Use of intramedullary intertrochanteric fracture fixation device 400 will now be described with reference to FIGS. 14-16. To assemble set screw assembly 444, a user may first couple split ring 466 to second member 464 by positioning the notch 496 of the split ring on the rim of the second member. The user may then thread the shaft 470 of first member 462 into the threading 490 of second member 464 coupling the first and second members together and sandwiching the split ring 466 between the neck 476 of the first member and the rim of the second member as shown in FIG. 15A.

Assembled set screw assembly 444 may then be inserted through the angulated opening 404 of intramedullary nail 402, fed into compartment 420 and moved in the distal to proximal direction until the neck 476 of first member 462 engages the upper ledge 448 of the compartment such that the neck is positioned within upper notch 474. If necessary, set screw assembly 444 may be rotated, before, during or after the set screw assembly is positioned within compartment 420 to ensure that the protrusion 492 of second member 464 is positioned within the slot 460 of the compartment.

With set screw assembly 444 pre-operatively assembled within the proximal portion 408 of intramedullary nail 402, the surgeon may insert a guidewire through the cannulated set screw assembly and advance the intramedullary nail 402 into position within the medullary canal 28 of the patient. After intramedullary nail 402 has been positioned within the medullary canal 28 of femur 10, the surgeon may then remove the guidewire and insert neck screw 406 through the angulated opening 404 of the intramedullary nail, as shown in FIG. 14, in order to compress the fractured bone portions together.

First member 462 may then be independently rotated relative to second member 464, allowing the surgeon to control the distance that intramedullary nail 202 is permitted to slide. Rotation of first member 464 causes the first member to rotate independently of second member 464 (which is rotationally stabilized by the engagement between the protrusion 492 of second member 464 the slot 460 of compartment 420) and results in the second member unthreading from the distal portion 470 of the first member, and separation of the first and second members.

As shown in FIG. 16, distal movement of second member 464 will cause the extensions 494 of the second member to extend into the angulated opening 404 of intramedullary nail 402 and to be received within a groove 436 of neck screw 406, thereby preventing the neck screw from rotating relative to the extensions of the set screw assembly. Neck screw 406 is thus prevented from rotating within angulated opening 404. Furthermore, as second member 464 moves in the distal direction and separates from first member 462, the first and second members will disengage from split ring 466 and the ring will radially expand into the upper notch 447 of compartment 420. It will be appreciated that the radial expansion of ring 466 aides in limiting the axial sliding of neck screw 406. For example, prior to the radial expansion of split ring 466, the neck 467 of first member 462 is permitted to slide axially within the upper notch 447. However, after the split ring 466 expands, proximal movement of set screw assembly 444 is limited by the engagement between the neck 476 of first member 462 and the upper ledge 448 of compartment 420, while distal movement of the set screw assembly is limited by engagement between the split ring and the lower ledge 450 of the compartment. As a result, axial movement of set screw assembly 444 is reduced, which in turn, reduces the permitted axial movement of neck screw 406.

The surgeon may then optionally fine tune the desired axial movement of neck screw 406 based upon individual considerations of a particular surgery. For example, if the surgeon desires to decrease the relative axial movement between neck screw 406 and intramedullary nail 402, the surgeon may insert a driving tool such as a hex key into the lumen 474 of first member 462 and rotate the first member in a first direction (e.g., counter clockwise) resulting in separation between the first and second members and an overall lengthening of set screw assembly 444. The lengthening of set screw assembly 444 results in the neck 476 of the first member pressing against the upper ledge 448 of compartment 420 and applying a counter-force to neck screw 406 via the extensions 494 of the second member. Conversely, if the surgeon desires to increase the amount of relative axial movement between neck screw 406 and intramedullary nail 402, the surgeon may rotate the driving tool in a second direction (e.g., clockwise). Clockwise rotation of first member 462 relative to the second member 464 will result in the distal portion 470 of the first member being threaded into the body 484 of the second member, thereby increasing the distance between the extensions 494 of the second member and the surface of the groove 436 of neck screw 406. Neck screw 406 will thus be permitted to slide relatively further in the axial direction.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A set screw assembly configured to be received within a compartment of an intramedullary nail, the intramedullary nail having an angulated opening for receiving a neck screw, the set screw assembly comprising:
a first member including a proximal portion and a distal portion extending along a longitudinal axis, the proximal portion including at least one flange being moveable in a radial direction relative to the longitudinal axis between an unlocked condition and a locked condition, the distal portion including a threading; and
a second member including a sidewall extending between a proximal end and a distal end, the sidewall defining an interior surface having a threading for threadably mating with the distal portion of the first member, the second member further including a lateral flange sized and configured to engage an interior surface of the compartment of the intramedullary nail for rotationally stabilizing the second member within the compartment.

2. The set screw assembly of claim 1, further comprising a third member insertable into the proximal portion of the first member and sized and configured to selectively transition the at least one flange between the unlocked and locked conditions.

3. The set screw assembly of claim 2, wherein the at least one flange includes a first flange and a second flange, each of the first and second flanges being moveable in the radial direction and between the unlocked and locked conditions.

4. The set screw assembly of claim 3, wherein the first and second flanges at least partially define a sidewall of the proximal portion and an interior surface of the sidewall of the proximal portion includes threading.

5. The set screw assembly of claim 4, wherein an external surface of the third member includes threading corresponding to the threading of the sidewall of the proximal portion such that threading the third member into the proximal portion of the first member transitions the first and second flanges to the locked condition.

6. The set screw assembly of claim 5, wherein an interior surface of the third member defines a plurality of recesses configured to receive a driving tool for threadably mating the third member to the first portion.

7. The set screw assembly of claim 1, wherein the distal end of the second member includes an extension configured to extend through the angulated opening and engage the neck screw.

8. The set screw assembly of claim 1, wherein the first member defines a non-circular recess configured to receive a driving tool for threadably mating the distal portion of the first member to the second member.

9. The set screw assembly of claim 1, wherein the first member and the second member are cannulated such that the set screw assembly is configured to receive a guide wire.

10. An intramedullary intertrochanteric fracture fixation device, comprising:
an intramedullary nail having a longitudinal axis, a proximal portion and a distal portion, the proximal portion defining an angulated opening and an axial bore extending through a proximal end of the intramedullary nail along the longitudinal axis and into the angulated opening, the proximal portion further having a compartment defined by an upper stop, a lower stop and a sidewall, the sidewall of the compartment defining a slot;
a neck screw extending through the angulated opening and having an exterior surface with a groove; and
a set screw disposed within the compartment of the intramedullary nail, the set screw comprising:
a first member including a proximal portion and a distal portion, the proximal portion including a plurality of flanges being moveable in a radial direction relative to the longitudinal axis between an unlocked condition and a locked condition, the plurality of flanges being annularly spaced from one another to define a first cavity;
a second member including a sidewall extending between a proximal end and a distal end, the sidewall defining a second cavity for receiving the distal portion of the first member, the second member further including an extension extending through the angulated opening and into a groove of the neck screw, and a lateral flange disposed within the slot of the compartment; and
a third member rotatably disposed within the first cavity such that rotation of the third member in a first direction transitions the plurality of flanges from the unlocked condition to the locked condition.

11. The set screw assembly of claim 10, wherein the first member, the second member and the third member are cannulated such that when the first member, the second member and the third member are coupled together the set screw assembly is configured to receive a guidewire.

12. The set screw assembly of claim 10, wherein the third member includes an interior surface defining a plurality of recesses annularly spaced about an interior sidewall of the third member for receiving a driving tool for driving the third member into the first cavity.

13. The set screw assembly of claim 10, wherein the third member is frustoconical in shape.

* * * * *